United States Patent

Becher et al.

Patent Number: 5,902,433
Date of Patent: May 11, 1999

[54] PROCESS AND A DEVICE FOR PRODUCING A TRANSDERMAL THERAPEUTIC SYSTEM FOR THE ADMINISTRATION OF ACTIVE SUBSTANCES TO THE SKIN IN THE FORM OF A PLANE MULTICHAMBER OR MULTICHAMBER-CHANNEL SYSTEM

[75] Inventors: Frank Becher, Koblenz; Walter Müller, Neuwied, both of Germany

[73] Assignee: LTS Lohmann Therapie-Systeme GmbH, Neuwied, Germany

[21] Appl. No.: 08/553,606

[22] PCT Filed: Apr. 25, 1994

[86] PCT No.: PCT/EP94/01278

§ 371 Date: May 2, 1996

§ 102(e) Date: May 2, 1996

[87] PCT Pub. No.: WO94/26346

PCT Pub. Date: Nov. 24, 1994

[30] Foreign Application Priority Data

May 19, 1993 [DE] Germany ............... 43 16 751

[51] Int. Cl.⁶ .................................................. A61M 37/00
[52] U.S. Cl. .................. 156/209; 156/220; 156/251; 156/292; 156/582; 424/448
[58] Field of Search ................................... 604/304, 307; 424/447, 448, 449; 156/290, 292, 581, 582, 583.1, 209, 219, 220, 251

[56] References Cited

U.S. PATENT DOCUMENTS

| | | | |
|---|---|---|---|
| Re. 34,692 | 8/1994 | Becher | 424/448 |
| 3,510,380 | 5/1970 | Bittner | 156/209 |
| 3,756,888 | 9/1973 | Kuroda | 156/209 |
| 3,867,225 | 2/1975 | Nystrand | 156/209 |
| 3,900,027 | 8/1975 | Keedwell | 604/307 |
| 4,357,935 | 11/1982 | Frantzill | 604/304 |
| 4,576,669 | 3/1986 | Caputo | 156/292 |
| 4,666,441 | 5/1987 | Andriola et al. | 604/304 |
| 4,701,235 | 10/1987 | Mitsam | 156/582 |
| 4,762,124 | 8/1988 | Kerch | 604/307 |
| 4,911,707 | 3/1990 | Heiber et al. | 424/449 |
| 4,917,676 | 4/1990 | Heiber et al. | |
| 4,990,144 | 2/1991 | Blott | 604/307 |
| 5,066,494 | 11/1991 | Becher | 424/448 |
| 5,376,203 | 12/1994 | Syme | 156/209 |
| 5,429,591 | 7/1995 | Yamamoto | 604/307 |
| 5,536,263 | 7/1996 | Rolf | 424/449 |

FOREIGN PATENT DOCUMENTS

| | | |
|---|---|---|
| 0 273 004 | 6/1988 | European Pat. Off. . |
| 3 642 931 | 7/1987 | Germany . |
| 3 722 775 | 1/1989 | Germany . |

*Primary Examiner*—Daniel Stemmer
*Attorney, Agent, or Firm*—Wenderoth, Lind & Ponack L.L.P.

[57] ABSTRACT

In a process for the production of a transdermal therapeutic system for the administration of active substances to the skin in the form of a plane multichamber or multichamber-channel system an active substance-containing layer is introduced between top layer and bottom layer; subsequently top and bottom layer are squeezed at individual and/or coherent sites under displacement of the intermediary sites of the active substance-containing layer and formation of active substance-containing chambers or channels, and at the same time or after that top layer and bottom layer are bonded permanently at the squeezed places.

40 Claims, 1 Drawing Sheet

PROCESS AND A DEVICE FOR PRODUCING A TRANSDERMAL THERAPEUTIC SYSTEM FOR THE ADMINISTRATION OF ACTIVE SUBSTANCES TO THE SKIN IN THE FORM OF A PLANE MULTICHAMBER OR MULTICHAMBER-CHANNEL SYSTEM

The present invention relates to a process and a device for the manufacture of a transdermal therapeutic system for the administration of active substances to the skin in the form of a sheet-like multichamber or multichamber-channel system.

BACKGROUND OF THE INVENTION

Transdermal therapeutic systems having chambers filled with active substances have been known for some time. In particular the transdermal systems initially placed on the market comprise chambers all filled with active substances. However, production of these systems is very expensive. In particular, the "membrane bags" which are filled with active substance must be produced individually in complicated process steps, and then be applied on suitable supporting sheets as a whole.

DE-OS 37 22 775 discloses a transdermal therapeutic system for the administration of active substances to the skin. It comprises a backing layer averted from the skin, an active substance depot, a control unit controlling the release of active substance by the system, and a pressure-sensitive adhesive device fixing the therapeutic system on the skin, the active substance depot being a multichamber system wherein discrete chambers comprise one or several active substances.

Special shaping of these systems, as is described in the above document, has not been possible as yet in an economically efficient manner. Another disadvantage lies in the fact that insufficiently subdivided chamber systems, when applied to vertical surfaces, tend to have an active substance mass accumulated at the lower edge resulting in a particularly intense supply into the skin at this point, whereas delivery in the upper part takes place to a considerably lesser extent. This can only be avoided—although imperfectly—by extremely thickening the active substance mass; however, this involves difficulties in the production of transdermal systems and limits the possibilities of design.

DESCRIPTION OF THE INVENTION

It is the object of the present invention to provide a very simple and thus cost-saving process by means of which the aforementioned transdermal therapeutic systems are manufactured in a simple manner and, as a result, at a comparatively high production rate. The universal possibilities of shaping the active substance-containing chambers or channels are intended to achieve the highest possible degree of freedom with respect to developing and forming new systems. Moreover, the process is intended to be particularly suitable for the use of liquid or semisolid active substance preparations, wherein it is in particular possible to dispense with mixing or thickening the active substance with adhesive masses; it is neither necessary to have the active substance absorbed by special materials which subsequently release the active substance again, for example, sometimes used in known nitroglycerin or nicotine patches. It is a further object of the present invention to provide a simple device particularly suitable for carrying out a continuous production process.

To achieve this object the present invention proposes to provide a suitable top layer and a bottom layer, to introduce an active substance-containing layer between these layers, and then to squeeze top and bottom layer at individual and/or coherent sites under displacement of the intermediary sites of the active substance-containing layer and formation of active substance-containing chambers or channels, and—at the same time or after that—to bond top layer and bottom layer permanently at the squeezed places.

Most advantageously the proposed process is simple and cost-saving, and it is suitable for universal possibilities of shaping the active substance islands embedded in chambers or channels as well as for the use of liquid active substances without having to provide them in a thickened form or together with absorbent materials.

According to an embodiment of the process the permanent bond of top and bottom layer is effected under the action of pressure, heat and/or ultrasonics.

According to another embodiment the permanent bonds are effected by gluing and/or welding top and bottom layer.

A particular advantage in the production of the system according to the present invention lies in the fact that the active substance mass may be applied on the whole surface. In contrast to matrix systems, it is not necessary to render the active substance layer comparatively viscous or solid by adding further substances, or to provide a tacky or adhesive-coated surface which ensures cohesion with other layers. It is not necessary to use expensive coating and metering systems in the manufacture of the system according to the present invention.

According to an embodiment of the present invention at least two layers having different active substances are introduced between top layer and bottom layer, and these active substances layers are divided into discrete chambers or channels having different active substances.

However, it is also possible to introduce between top layer and bottom layer at least two layers having active substances with different degrees of saturation or concentrations, and to divide these active substance layers into discrete chambers or channels having active substances of different degrees of saturation or concentrations.

In this connection it is to be emphasized that the form of the reservoir chambers or surfaces, which in combination with the active substance mass permit a high degree of freedom in the conception of transdermal systems, is a special advantage of the unlimited shaping possibilities, but that this is particularly true for the possibility of using different layers of active substance or of producing several active substance chambers separated by membranes and having different saturation degrees.

Another advantage lies in the fact that the active substance can also be applied in the form of capsules by means of roller coating so that highly toxic substances can be applied without endangering the personnel, and that these capsules may also be completely lightproof so that even light-sensitive active substances may be processed without any difficulty.

According to an embodiment a web of a coated membrane sheet or one to be coated is used as bottom layer, and a web of a supporting material which is completely or selectively coated with an adhesive is used as top layer.

The application of active substance as well as that of the adhesive may also be effected according to a given pattern by means of a technique substantially corresponding to gravure printing. The webs are manufactured from of a suitable material known to the skilled artisan, i.e.

1. a membrane web (supporting web), referred to as bottom or lower web in the following and
2. a cover web or top web.

Depending on the respective embodiment the position as the top or bottom web may be exchanged. The membrane web may be produced, for example, by applying a layer of a skin-compatible adhesive, which is permeable to the active substance, on a supporting layer simultaneously assuming the cover function—e.g., a silicone sheet. This adhesive layer is laminated with a web suitable for the use as membrane. The adhesive is a conventional solvent-based or hot-melt adhesive rendered spreadable by means of heating. If solvent-based adhesives are used, the solvents must subsequently be removed by drying. The top web is made, for example, of a conventional active substance-containing supporting sheet by applying on said substrate an adhesive that is spreadable in hot condition (preferred temperature range about 50–100° C.) but becomes solid below said temperature range and is no longer tacky. Although it is advantageous to provide both webs with a pressure-sensitive adhesive, it may be sufficient to provide only one web with the adhesive, in particular the top web. Instead of applying the adhesive all over the surface, both webs may also be coated with the adhesive in the form of a net, lines, or spots; this in particular applies to the membrane web. This ensures that the active substance passage—if desired—is not impaired beyond the necessary degree. This particularly applies to the production of multilevel systems. The substrate of the top web consists of a conventional sealable material, e.g., polyethylene vinyl acetate or polyethylene vinyl alcohol.

During production the lower web is placed in a coating line and coated with the active substance-containing liquid mass, appropriately over the whole surface. Depending on the requirements, a solvent—including water—may be added to this mass to improve the spreading properties, the solvent being removed by subsequent drying.

According to an embodiment the bottom web thus manufactured is laminated with the top web in a further process step. A stable composite may be produced by using heated embossing punches giving the reservoirs and channels the intended shape. This can be effected by providing raised portions in the form of spots or a screen in the total surface of the punch. This punch is applied at a defined pressure on laminated, but not yet firmly connected webs so that the active substance mass, which suitably is in a semiliquid form, is displaced at the points of contact. Immediately after application or from the beginning, the punch is heated such that the hot-melt adhesive melts and thus bonds bottom and top web. Depending on the shape of the punches the finished patches are stamped later in the usual manner.

According to an embodiment a web of a conventional, active substance-containing supporting sheet is used as top web, and an adhesive is applied thereon which is spreadable in hot condition, preferably in a temperature range between 50 and 100° C., but becomes solid below said temperature range and ceases to be sticky.

When selecting the sheeting materials, it is important that they have a certain compressive strength and temperature resistance. The pressure resistance depends on the viscosity of the active substance mass and the punch pressure necessary to create a fixed bond by means of heated punches. The desired temperature resistance of the sheets depends on the temperature heating the punches; i.e., a temperature and pressure-induced change of the sheets must be avoided. On the other hand, they must have the required elasticity which permits to compensate the volume reduction caused by gluing.

These production methods have been regarded as impracticable so far. In the past, it appeared impossible to displace the applied active substance mass at the surface portions to be bonded to a sufficient degree. Experts believed that residues of the active mass would remain at the joints, exerting an external action rendering a reliable glue or weld impossible. This prejudice has proven to be incorrect. In tests carried out with two sheets between which the liquid Mybiol—a usual additive for transdermal systems—had been applied, a reliable bond of top and bottom layer could be achieved after a simple displacement by means of the pressure exerted by the welding tongs.

According to an embodiment energy is used to heat the hot-melt adhesive, for example microwave radiation, infrared radiation; microwave, infrared, or x-ray lasers; or a combination of these forms of radiation.

This embodiment ensures that the energy causing the heating is transferred as evenly as possible.

It reduces the effect that the cover sheet is excessively heated during heat transfer from the embossing punch. Thus even heating of the sealing material is ensured.

According to an embodiment the substrate thus produced, in particular the points of bond, is cooled, preferably in a quick manner, immediately after top layer and bottom layer have been bonded by means of heating. This prevents that the active substance mass and the other patch components are subjected to a harmful effect caused by the temperature elevation.

A device for producing a transdermal therapeutic system for the administration of active substances to the skin in the form of a plane multichamber or multichamber-channel system, in particular for carrying out the process according to the present invention, is characterized by the fact that it has means for squeezing individual or coherent points of the top layer and bottom layer, said means being provided with contact-bearing pressure-surfaces which spare the chambers or channels enclosing the active substance and being formed as punches or rolls.

According to a preferred embodiment the contact surfaces of said punches may have a rounded and/or ellipsoidal form to achieve a desired distribution of the active substance mass in the whole patch. A slightly rounded form of the contact surfaces is useful, it achieves a contact in the middle of the contact surface first, which then spreads over the whole bearing surface. According to a preferred embodiment the support is flexible. Displacing the active substance-containing, suitably semiliquid mass into the resulting accommodation spaces is thereby facilitated, whereby a complete contact between hot-melt adhesive layer and the layer to the bonded is formed and successful bonding results.

According to a useful embodiment the bearing pressure surfaces of the punches or rolls are heatable.

According to another embodiment two groups of punches or embossing rolls are arranged in series in a production line, which preferably operates in continuous mode, and have corresponding embossing structures; the first group being formed to squeeze the layers of the substrate, and the following group being provided with heated contact surfaces to bond these layers.

In this embodiment the first punch group assumes the function of displacing the active substance in the web from those surfaces where the two webs are to be bonded. The second punch, which is virtually placed upon the same contact points, then forms the bond by heating the pressure-sensitive adhesive through the cover sheet, thus producing a joint. In this embodiment the second punch group is heated.

Embossing rolls may also be used instead of embossing punches. Their cavities may preferably be provided with bores to create the required pressure compensation. A suitable shape of the embossing rolls may completely displace the active substance into the chambers, preventing waste of active substance.

According to a preferred embodiment of the punches, their contact surfaces consist of a material which is transparent to energy whereby a slot which is transparent to energy is formed. In contrast to this, the cavities are formed of a reflecting material. When these punches are led onto the bottom web, they displace the active substance below the contact surfaces first. Subsequently, they approach a section wherein energy waves, such as microwaves or infrared radiation, are continuously created in and emitted from a radiation chamber. These rays may also be employed in the form of beams or lasers, e.g. as x-ray lasers. When the energy-transparent slot of the punch with the webs squeezed together passes over the contact surface, the energy wave passes through the transparent contact surface and causes short-term heating immediately ceasing as soon as the following section is reached. As for the rest, the chambers are made of an opaque material such as metal, therefore the action is limited to the web portion affected by the gap. In a preferred embodiment such a chamber may be arranged at the top and at the bottom to ensure even heating of the bond points.

According to another preferred embodiment the microwave radiation is amplified resulting in a so-called "maser". In this connection, it is preferable to trap beams for measuring purposes, and to use the result for measuring and controlling purposes for an "inprocess testing" to obtain indications with respect to layer thickness and specific compositions at the test points.

Another preferred embodiment consists in the fact that the required temperatures are created by applying ultrasonics to the punch unit (punching roll or embossing punch).

According to an embodiment one punch or embossing roll is provided, in addition to their contact surfaces, with punching or cutting tools to manufacture webs into individual substrates. In the forming process it is thus possible to decide whether the punches are to effect blanking, or whether the corresponding webs are to be cut into smaller webs which are punched in a subsequent processing step. For example, the embossing rolls may merely be provided with a knife or punch acting in the longitudinal direction. However, it is also possible that both embossing rolls and punches simultaneously assume the function of a cutting die. An embodiment of the device, which is an essential of the present invention, consists in the fact that the embossing punches or embossing rolls are provided with means for applying a vacuum. The vacuum acts on the active substance-containing layer, with the consequence that it is sucked into the cavities resulting during embossing and is taken off the contact surfaces.

A possible embodiment of the device for applying a vacuum may consist in forming the punch of a system comprising a stationary piston with a cylindrical shaft. When the shaft moves, a cavity and thereby a vacuum is formed whereby the sheet is drawn into the cavity of the shaft.

In another preferred embodiment the vacuum is changed into an excess pressure after the bond has been effected in order to facilitate removal of the joined webs from the punches.

By combining the various embodiments, the device according to the present invention may put a logical production method in operation. For instance, the assembled layers or webs are conveyed by means of a transport device below the embossing punch or below the embossing roll, the punch or roll carries out a downward stroke, sucks the sheet and thereby displaces the active substance, bonds by means of heating, cuts the patch by means of the cutting knives provided at its edges, detaches from the transportation web as a result of the vacuum, lifts it and, because of the abrupt change from vacuum to excess pressure, "spits" it onto another conveying belt arranged between top web and bottom web which at this point are guided in an upward or downward angle in such a manner that space for the conveyor belt is provided between them.

The aforementioned upper rolls are suitably passed over lower rolls so as to ensure continuous feed and removal of the webs to be bonded. Both the upper and the lower roll may be provided with corresponding embossed designs which meet at the moment of bonding, thus ensuring an embossed print on the contact points of the punches. The lower roll may comprise indentations for optional cutting knives to permit clean cut-off. In addition, a vacuum may be applied to the upper roll so that cavities are formed in the upper and the lower web, into which the active substance mass is displaced from the contact surfaces.

Moreover, the bottom side of the embossing and displacement punches may be combined with a corresponding punching bed which also has embossed designs and—according to a preferred embodiment—is also provided with a vacuum.

It is also possible to arrange the embossing punches on a rotating belt, a link chain, and the like in the manner of a crawler-type vehicle. They are pressed at a defined pressure, for example, by means of rollers or similar devices.

Another embodiment of the device provides that the same device is arranged at the bottom side, optionally provided with a corresponding counter punch and, if necessary, a vacuum.

A stationary "embossing bed", as used in the production of block prints may serve as an alternative to a movable punch or a corresponding roll, or to a rotary belt provided with a punch, or a rotating chain or the like. These embossing beds may be provided with a bore to apply a vacuum. In the first step, the web is guided onto the embossing bed, a vacuum is applied so that cavities are formed, at the same time a flat punch moves onto said bed and displaces the active substance preparation at the contact surfaces of the embossing bed, thus filling the chambers. The "embossing bed" may also be attached to a rotating belt; the flat punch may be replaced by a roller or a corresponding rotary belt.

The device may also be formed such that the punches are not guided at right angles to the web to be embossed, but are mounted on a roller; in principle resembling the rollers used in the household to form breads and pastries (rolls for biscuit molding). The particular advantage of this embodiment lies in the fact that the active substance mass is displaced into the resulting reservoirs on the one hand, but what is more, it is also moved in front of the roll's contact point in a form similar to a "wave", thus being used intelligently. This reduces occurrence of material tensions.

Another embodiment consists in using two rolls—corresponding to the two punch groups—which influence the forming. In this connection, the first roll assumes the function of displacing the active substance from the contact points, and the second one that of causing the firm bond by means of heating.

A preferred embodiment of the embossing punch or roll consists in giving the reliefs thereof a hollow shape, and applying a vacuum to said relief the moment the embossing punch contacts the upper sheet. The upper sheet is thereby drawn into the reliefs of the embossing punch to a defined extent and prestressed. This results in a vacuum between upper and lower sheet whereby the active substance is drawn from the contact surfaces towards the respective middle of the chamber and channels so that the displacement effect at the contact surfaces is promoted.

Additionally, it is possible to provide the cover sheet, prior to joining it with the active substance sheet, with a sheet for deep drawing—however with an only slighter depth—in a similar process; to this end, it is laminated over the male-female-punches of an embosser with a sealing sheet. This may preferably be carried out similar to a gravure coating method as follows:

The punches or roll-type punches which are provided with reliefs are running in a heated roll. The reliefs are filled with hot-melt adhesive, and the raised portions are cleaned by means of a knife; subsequently, the roll and the sheet (upper web) are converging and the adhesive is supplied to the exactly defined bond surfaces on the sheet. To avoid bonding of the hot-melt adhesive with the punch or punching roll, these are coated adequately, preferably with silicone preparations such as polytetrafluoroethylene. This may also be effected after having coated them with a hot melt adhesive.

It is also possible, however, that the processing step is carried out prior to applying the active substance mass by means of a heated roll; in this case only the raised contact points are advantageously coated with the hot-melt adhesive. Instead of a hot-melt adhesive, a suitable sealing medium may also be used; during feeding it is given adhesive properties by means of heat, and it loses said adhesive properties on returning to normal temperature conditions.

According to a preferred method the active substance is applied in the embossed reservoir spaces in the manner of a gravure printing process or of another suitable printing process. This may be effected via the cavities of another roll system—as in gravure printing. In a subsequent processing step the fixed bond would then be effected according to the above-mentioned principles, following the application of active substance which is not spread over the whole surface in this case.

The method may be modified such that the active substance is applied as described above, however not into preembossed cavities but in the form of a surface coating. Since there is a small amount of active substance mass, it is in many cases not necessary to provide a relief. The elasticity of the sheet will then be sufficient to ensure formation of the desired cavities after solidification by means of the heat sealing process.

In an all-over application, the punch does not perform a displacing function, and with respect to the device only one punch or the punching roll (which may be a cutting roll at the same time) is required.

It may be useful to coat the contact point with the hot-melt adhesive also in the manner of a gravure printing method via a corresponding roller on the later bond points, and to apply the active substance after that. The reversed order is possible too.

If the supporting sheet is not coated with hot-melt adhesive, small pieces of hot-melt adhesive, e.g., in the form of spheres, may instead be mixed with the active substance mass during preparation thereof, and they may then be applied together.

When the embossing punch (optionally roll or rotary belt) approaches the support from the top, a portion of the mass with the spheres is displaced first; since these are solid many of them remain in the contact surface. This results in an increased specific pressure on the—small—contact surfaces, which improves the displacement of the active substance mass; it can flow off in the interspaces in a particularly good manner. Through heating by means of the punch, the hot-melt adhesive particles become pasty or liquid and combine with the upper and lower sheet so that a bond results. Preferably, (micro)encapsulated conventional adhesives may also be used, these are added to the active substance mass and applied as mentioned above. In this case there is no need for a heated punch to effect the bond. After a major portion of the active substance mass has been displaced to a larger extent because of the relatively stronger "hardness" of the capsules, the capsules will burst by the mere pressure exerted by the punch.

A modification of the method provides that a mass consisting of conventional adhesives and microencapsulated further adhesive layers is applied by means of a gravure printing process to the lower web (support) at the positions later serving as the fixation points. If the adhesives contain solvents, these are dried in a conventional manner. Therefore relatively solid adhesive particles stick to the later bond areas under the supporting sheet. During embossing these ensure that the active substance is displaced first. In an end phase the capsules will burst and cause the bond. This method can therefore also be used for temperature-sensitive active substance masses. As compared to a single coating, the advantage lies in the fact that the active substance mass does not combine with the adhesive and therefore does not produce an intermediate layer preventing a connection with the lower membrane sheet. In one or several operations according to the aforementioned processes small, encapsulated, conventional adhesive particles may be applied on the defined surface at the later bond points by means of a suitable, quick-drying solvent-based adhesive. In this case, fixation may be effected by merely exerting the corresponding pressure. This pressure displaces the active substance mass probably being present below first; in a further phase the microcapsules burst and release the adhesive which then causes a solidification between top and bottom web.

A particular advantage of the present invention lies in the fact that production and development may be standardized to a great extent, and that most of the components may be reduced to a few types that can be prefabricated.

For instance, it may well be sufficient to coat a few membrane types of different permeability; and only few different adhesives must be selected for the respective membrane.

The conditions are even better in case of the top web, which may always be the same for the most diverse transdermal therapeutic systems, since it must only be leak-proof and compatible with the active substance mass. The requirements for these components are so modest that a GMP-production of these components is not necessary.

The punches are also universal.

As compared with the known bag patches, the present invention has the advantage that there is no "bulging" at vertical surfaces, and that an even concentration is present in the upper region too. For this reason the process is particularly suitable if liquid or semiliquid active substance preparations are to be used whose application in connection with adhesive masses is problematic, for example, because of poor miscibility, loss of adhesive force, etc. It is particularly suitable if rapid diffusion through the membrane—unimpeded by the adhesive—is desired, because safe attachment is nevertheless achieved by the fact that the surfaces below the "channels" are kept free from active substance and are retained by the adhesive surfaces between the "channels".

Another advantage of the present invention lies in the possibility of using semifluid masses whose active substance has a stronger maceration action. This can be reduced by forming the chambers comprising the active substance in such a manner that the actual adhesion points at the bonding sites are kept free from active substance. Thus a "screen" or "lattice" of contact surfaces may be formed, on which the active substance acts on the skin. This requires a larger surface of the patch, but the advantages thus obtained compensate for this.

The process according to the present invention proves to be particularly advantageous if the active substance mass tends to react ("temper") with the adhesive under certain temperature conditions. For instance, selegiline hydrochloride is known to react with the basic components of an acrylic adhesive, so that selegiline base is formed which does not have the properties desired for the transdermal application.

If a multichannel system is used, an acrylic adhesive need not be used, and the skin contact of the active substances can be achieved without any adhesive.

In the development of "screening" the skin permeability of active substances, the process according to the present invention works out to great advantage; in the development of transdermal systems it helps to gain first findings.

Different active substance masses may rapidly be combined with prefabricated components, and corresponding patches may be manufactured according to the present invention, for example, by means of a simple coater equipped with a heated roll. Troublesome determination of suitable mixtures of adhesives with active substance masses is no longer necessary, the same applies to the search for a suitable absorbent material, such as nonwovens.

EXAMPLES

Figure 1:
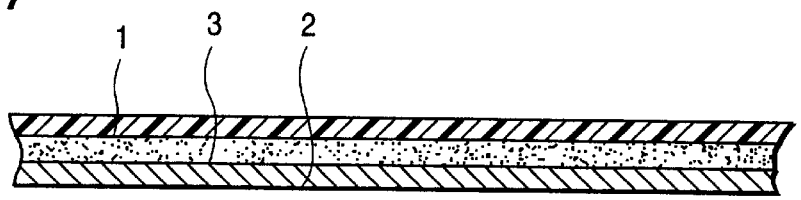
FIG. 1 shows the initial situation, i.e., the presence of a substrate having a top layer (1) and a bottom layer (2) and the active substance-containing layer (3)
Figure 2:
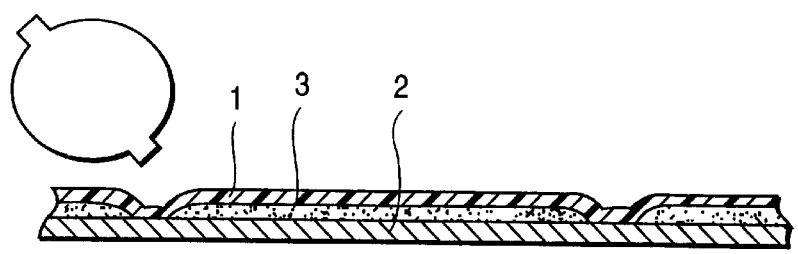
FIG. 2 shows the beginning of the process according to the invention, with a stylized representation of the roll for connecting the top layer with the bottom layer.
Figure 3:
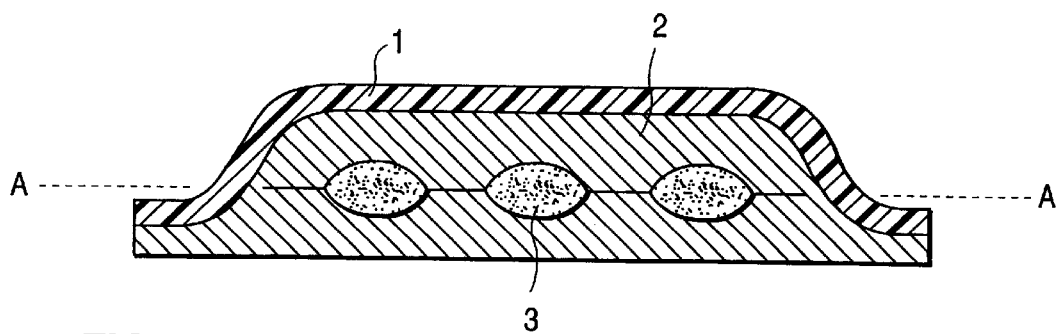
FIGS. 3 and 4 show the product of the process in cross-section as well as in longitudinal section (FIG. 4) along the line A—A shown in FIG. 3.
Figure 4:
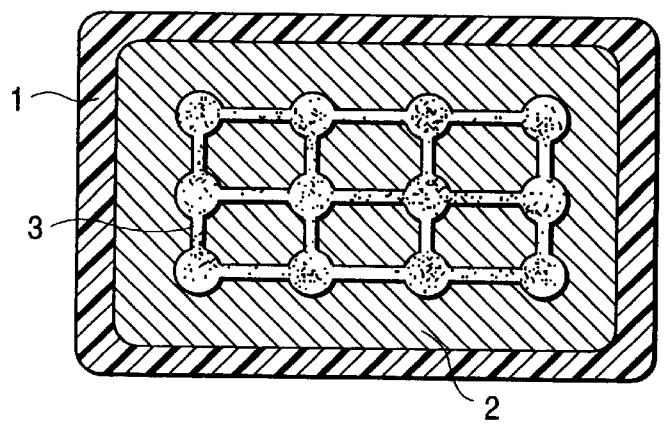

1. A mass with an active substance preparation is applied on the surface of a bottom web (membrane). The bottom web and a top web are laminated and supplied to the bonding station; the top web is obtained by coating a cover sheet with a skin-compatible hot-melt adhesive which is permeable to active substances and laminating a membrane sheet which permits passage of the active substance in a controlled manner. The bonding station consists of a first storage section, a feeding section, a bonding section, a conveying section, a second storage section, and the transporting section. The laminated web which is not connected firmly because of the intermediate layer of active substance mass is supplied to the storage position. Behind the storage place, it is retained and stretched by the clamping unit of the feeding place and—at the same time—by the conveying section. The bonding area is arranged behind the feeding section. In said bonding section a displacement punch, which displaces the active substance at the embossing contact surfaces, is guided on the webs first. Through a transport movement of the whole transport device, the sheet is passed on to the actual bonding place. Here a heated embossing punch is exactly guided onto the same places where the preceding displacement punch has displaced the active substance between the sheets. Depending on the adhesion, cohesion, and viscosity of the active substance mass, the contact surface of the heating punch is slightly smaller than that of the displacement punch, during the interim transportation step the active substance mass is thus prevented as far as possible from flowing back to its previous position.

The heating punch permanently fixes the system at different points by rendering the hot-melt adhesive or a sealing sheet located between the supporting sheet and the bottom web adhesive. In a further transport step, the sheet with the structured systems is conveyed to the storage section and further to the transport roll, later individual pieces are packaged.

2. Bottom web and top web are laminated and supplied to the bond station as in Example 1. Contrary to Example 1, the displacement operation and the bonding operation are carried out in one step; i.e., the bonding punch is heated and—in one process step—displaces the active substance mass between the two webs and retains the hot-melt adhesive layer, so that top and bottom webs bond together at the contact surfaces.

Displacement and bonding step may be carried out in partial steps by initially guiding the punch such that mere displacement takes place, and exerting further pressure after a short time—i.e., after the result is achieved—so that bonding is effected under pressure. In this connection, the second partial step may be carried out such that the bottom web is guided against the punch via a rotary knob. This alternative has the advantage that possible tensions of the sheet distribute evenly on the bottom web and the top web, so that the finished systems do not bend because of different tension conditions.

3. The same procedure as in Example 1 or 2 is carried out, with the proviso that the bonding punch is also used to cut the patches into individual pieces by forming sharp-edged borders like in a cutting die; the blades may be formed to engage into corresponding slots on the bearing area by means of pressure, so that a clean cut is obtained.

4. Procedure is as in Example 2. Instead of a displacement punch and a bonding punch, or a combined punch, optionally equipped with stamping blades as in Example 3, rotary punching rolls—in the form of rolls for biscuit molding used for baking—are used. This has the advantage that storage section and feeding device are not necessary—the upper punching roll may be heated. An advantageous modification may be obtained by effecting displacement and/or bonding by means of an upper roll which is combined with a suitably formed lower roll. The lower roll may be formed such that is has knob-shaped raised portions at suitable places to enhance displacement and bonding in two different sections. A separate feeding member is not necessary in this case, or it may be formed in a simpler manner. The displacement/bonding roll may have the form of a cutting die, also combined with a corresponding lower roll. In addition, take-off devices may be provided for the finished patches.

5. A top web and a bottom web are produced, and both are joined as described in Examples 1 and 2; however, the top web is not coated with the hot-melt adhesive all-over, but in the manner of a printing process by means of a heated gravure printing cylinder rotating in a heated pan. The cylinder is provided with slight depressions that are doctored by means of a knife. Subsequently, hot-melt adhesive is passed on the web and sticks thereon. In this process the desired patterns for hot-melt adhesive points and reliefs for the pasty active substance mass may be provided.

The active substance mass may be applied in correspondingly complementary patterns, optionally onto the upper web—from below. In this case, the active substance mass is adjusted such that viscosity and adhesion, cohesion and tackiness are sufficient to retain the active substance on or below the sheet up to bonding. The other steps of bonding are carried out as mentioned above. The same applies to cutting into individual pieces.

6. Two webs are produced again. However, the supporting sheet previously located at the top is now placed at the bottom. At first, hot-melt adhesive is applied to the desired fixing points in defined portions by means of a process similar to gravure printing. This process is carried out with the sheet turned, i.e., on the side which will subsequently lie at the top above the sheet, instead of lying at the bottom below the sheet. The hot-melt adhesive is applied—optionally in several steps—at a thickness permitting the formation of channels and chambers according to the present invention between the adhesive points. These chambers are then coated with active substance all-over—at the contact points of the hot-melt adhesive excess active substance is removed by means of a knife.

The process of solidification is carried out according to a process of the above Examples, with the proviso that only a bonding step and no displacement step is necessary.

7. The production is carried out as in Examples 1 to 6, however, a supporting sheet is used which is suitable for deep drawing, thus obtaining the desired indented and raised portions by means of an embossing punch or corresponding embossing rolls. These indented and raised portions are coated with hot-melt adhesive or microcapsule adhesive in accordance with Examples 1 to 6, filled with active substance mass, bonded, and optionally taken off in cut form.

We claim:

1. A process for the manufacture of a transdermal therapeutic system for the controlled administration of active substances to the skin, said transdermal therapeutic system comprising:
   a top layer,
   at least two chambers containing active substance, said chambers being in communicational relationship by means of at least one active substance containing channel, and
   a bottom layer which is permeable to the active substance;
   said process comprising:
   (1) preparing a laminate comprising a top layer, an active substance containing reservoir layer and a bottom layer,
   (2) squeezing predetermined sites of said top layer onto said bottom layer thereby displacing said active substance containing reservoir layer,
   (3) permanently bonding said top layer and said bottom layer with each other at said squeezed sites, and thereby forming two or more chambers containing active substance and one or more active substance containing channel for causing said communicational relationship between said chambers, and
   (4) cutting the resulting laminate into said transdermal therapeutic systems;
   wherein the steps of said squeezing, said bonding and said cutting are carried out simultaneously by means of a single embossing punch or embossing roller with a surface having rounded elevations for exclusively squeezing said predetermined sites and a cutting knife for cutting the outer contours of said transdermal therapeutic systems.

2. The process of claim 1 wherein the permanent bonding of said top layer and said bottom layer is effected by means of one of the action of pressure, heat, ultrasonics, gluing, welding or by a combination of at least two of said means.

3. The process of claim 1 wherein the permanent bonding of said top layer and said bottom layer is effected by a combination of pressure and heat.

4. The process of claim 1 wherein said reservoir layer comprises at least two different active substances having different concentrations or different saturation degrees.

5. The process of claim 1 wherein said reservoir layer comprises at least two layers, each of said layers comprising a different active substance, said process forming separate chambers and channels for each of the at least two different active substance reservoir layers.

6. The process of claim 1 wherein said bottom layer is a membrane layer.

7. The process of claim 1 wherein said bottom layer comprises an adhesive.

8. The process of claim 7 wherein said bottom layer comprises a pressure sensitive adhesive.

9. The process of claim 8 wherein said pressure sensitive adhesive is a hot melt pressure sensitive adhesive.

10. The process of claim 1 wherein said top layer is impermeable to the active substance.

11. The process of claim 1 wherein said top layer comprises a pressure sensitive adhesive.

12. The process of claim 11 wherein said pressure sensitive adhesive is a hot melt pressure sensitive adhesive.

13. The process of claim 1 wherein said top layer is completely or partially covered by an adhesive layer.

14. The process of claim 1 wherein said bottom layer is completely or partially covered by an adhesive layer.

15. The process of claim 1 wherein the preparation of said laminate is effected by application of a gravure printing technique of an active substance containing formulation with a given pattern onto said top layer or onto said bottom layer.

16. The process of claim 1 wherein the active substance containing reservoir layer of said laminate comprises a pressure sensitive adhesive.

17. The process of claim 16 wherein said pressure sensitive adhesive is a hot melt pressure sensitive adhesive.

18. The process according to claim 15 wherein said pattern has the form of a net, lines or spots.

19. The process according to claim 17 wherein said hot melt adhesive is heated by means of microwave radiation, infrared radiation or x-ray laser irradiation or combinations thereof.

20. The process of claim 1 further comprising cooling of said squeezed sites.

21. A process for the manufacture of a transdermal therapeutic system for the controlled administration of active substances to the skin, said transdermal therapeutic system comprising:
   a top layer,
   at least two chambers containing active substance, said chambers being in communicational relationship by means of at least one active substance containing channel, and
   a bottom layer which is permeable to the active substance;
   said process comprising:
   (1) preparing a laminate comprising a top layer, an active substance containing reservoir layer and a bottom layer,
   (2) squeezing predetermined sites of said top layer onto said bottom layer thereby displacing said active substance containing reservoir layer, (3) permanently bonding said top layer and said bottom layer with each other at said squeezed sites, and thereby forming two or more chambers containing active substance and one or more active substance containing channel for causing said communicational relationship between said chambers, and (4) cutting the resulting laminate into said transdermal therapeutic systems;

wherein said steps of squeezing and bonding of said top layer and said bottom layer are carried out in chronological order by means of a first embossing punch or embossing roller with a surface having rounded elevations and a second embossing punch or embossing roller with a surface having elevations that are heatable.

22. The process of claim 21 wherein the permanent bonding of said top layer and said bottom layer is effected by means of one of the action of pressure, heat, ultrasonics, gluing, welding or by a combination of at least two of said means.

23. The process of claim 21 wherein the permanent bonding of said top layer and said bottom layer is effected by a combination of pressure and heat.

24. The process of claim 21 wherein said reservoir layer comprises at least two different active substances having different concentrations or different saturation degrees.

25. The process of claim 21 wherein said reservoir layer comprises at least two layers, each of said layers comprising a different active substance, said process forming separate chambers and channels for each of the at least two different active substance reservoir layers.

26. The process of claim 21 wherein said bottom layer is a membrane layer.

27. The process of claim 21 wherein said bottom layer comprises an adhesive.

28. The process of claim 27 wherein said bottom layer comprises a pressure sensitive adhesive.

29. The process of claim 28 wherein said pressure sensitive adhesive is a hot melt pressure sensitive adhesive.

30. The process of claim 21 wherein said top layer is impermeable to the active substance.

31. The process of claim 21 wherein said top layer comprises a pressure sensitive adhesive.

32. The process of claim 31 wherein said pressure sensitive adhesive is a hot melt pressure sensitive adhesive.

33. The process of claim 21 wherein said top layer is completely or partially covered by an adhesive layer.

34. The process of claim 21 wherein said bottom layer is completely or partially covered by an adhesive layer.

35. The process of claim 21 wherein the preparation of said laminate is effected by application of a gravure printing technique of an active substance containing formulation with a given pattern onto said top layer or onto said bottom layer.

36. The process of claim 21 wherein the active substance containing reservoir layer of said laminate comprises a pressure sensitive adhesive.

37. The process of claim 36 wherein said pressure sensitive adhesive is a hot melt pressure sensitive adhesive.

38. The process according to claim 35 wherein said pattern has the form of a net, lines or spots.

39. The process according to claim 38 wherein said hot melt adhesive is heated by means of microwave radiation, infrared radiation or x-ray laser irradiation or combinations thereof.

40. The process of claim 21 further comprising cooling of said squeezed sites.

* * * * *